United States Patent
Lee et al.

(10) Patent No.: US 7,578,792 B2
(45) Date of Patent: Aug. 25, 2009

(54) AUTOMATIC OPTIMIZATION IN SPECTRAL DOPPLER ULTRASOUND IMAGING

(75) Inventors: Chi-Yin Lee, Bellevue, WA (US); Paul Donald Freiburger, Issaquah, WA (US); Mark G. Magrane, Redmond, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1216 days.

(21) Appl. No.: 10/624,120

(22) Filed: Jul. 21, 2003

(65) Prior Publication Data

US 2005/0033175 A1 Feb. 10, 2005

(51) Int. Cl.
*A61B 8/00* (2006.01)
(52) U.S. Cl. .......................... 600/453; 600/455; 600/437
(58) Field of Classification Search ................ 600/453, 600/437, 455
See application file for complete search history.

(56) References Cited

U.S. PATENT DOCUMENTS

| | | | |
|---|---|---|---|
| 4,644,795 A | 2/1987 | Augustine | |
| 4,937,797 A | 6/1990 | Snyder et al. | |
| 5,299,174 A * | 3/1994 | Forestieri et al. | 367/135 |
| 5,365,929 A | 11/1994 | Peterson | |
| 5,476,097 A * | 12/1995 | Robinson | 600/441 |
| 6,176,830 B1 * | 1/2001 | Freiburger | 600/453 |
| 6,251,077 B1 * | 6/2001 | Mo et al. | 600/455 |
| 6,322,509 B1 * | 11/2001 | Pan et al. | 600/443 |
| 6,390,984 B1 | 5/2002 | Pan et al. | |
| 6,577,967 B2 * | 6/2003 | Mo et al. | 702/76 |
| 6,733,454 B1 * | 5/2004 | Bakircioglu et al. | 600/453 |
| 2003/0045797 A1 * | 3/2003 | Christopher et al. | 600/453 |

FOREIGN PATENT DOCUMENTS

EP 0 985 380 A1 5/1997

* cited by examiner

*Primary Examiner*—Long V Le
*Assistant Examiner*—Jacqueline Cheng

(57) ABSTRACT

Methods and systems for automatic optimization in spectral Doppler ultrasound imaging are provided. The value for one or more spectral Doppler parameter is optimized using numerical optimization rather than predefined sampling. Various spectral Doppler parameters are set, such as a position of the gate, gate size, transmit frequency, filter settings, Doppler gain, beamline orientation or angle of intersection between the gate position and the scan line, aperture size, or other spectral Doppler transmit or receive parameters effecting the spectral Doppler imaging. A processor automatically calculates a setting or value for one or more of the spectral Doppler parameters, resulting in more objective optimization than provided by a user setting.

16 Claims, 2 Drawing Sheets

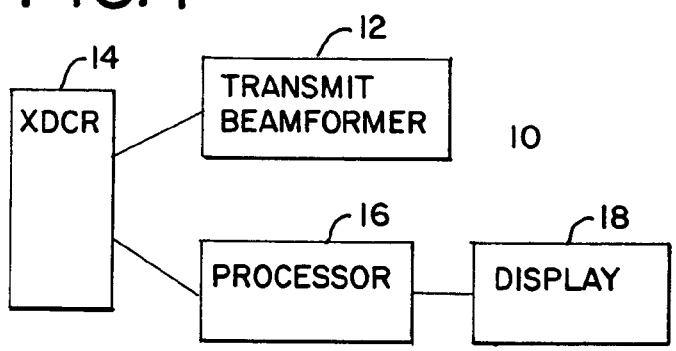
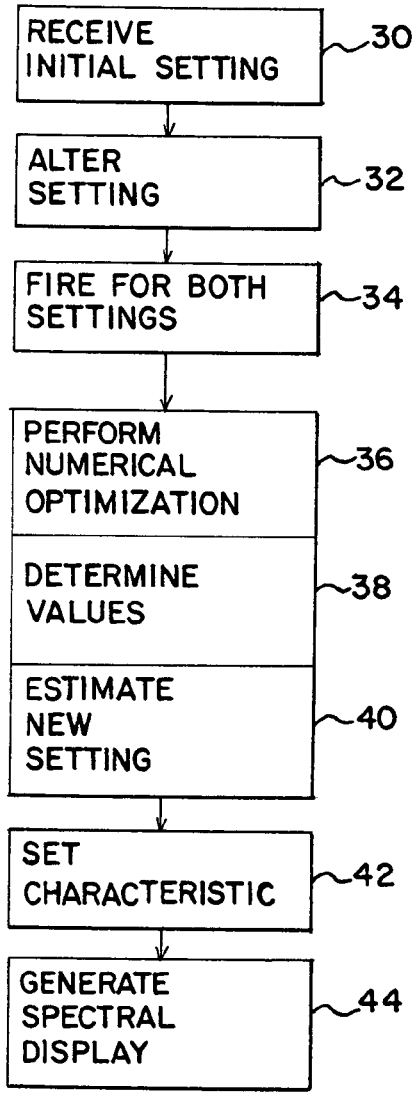
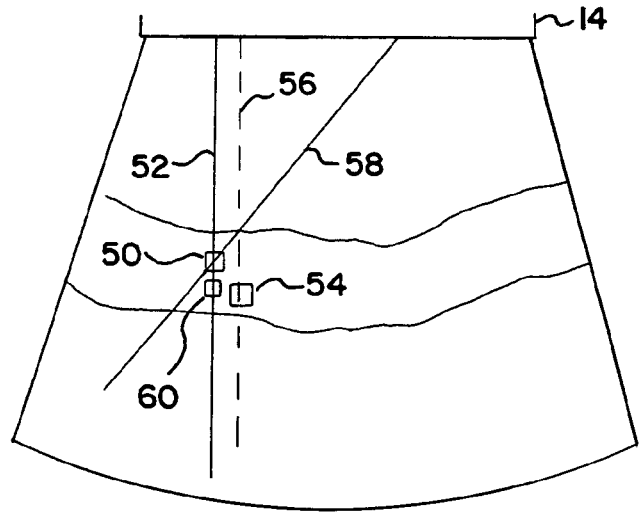

AUTOMATIC OPTIMIZATION IN SPECTRAL DOPPLER ULTRASOUND IMAGING

BACKGROUND

The present invention relates to spectral Doppler ultrasound. In particular, automatic optimization of spectral Doppler ultrasound imaging is provided.

Spectral Doppler ultrasound imaging provides a two-dimensional image of velocities (vertical scale) values modulated by energy as a function of time (horizontal scale) for studying fluid flow within a patient. By transmitting a plurality of pulses at a single gate location, a spectral Doppler response is generated in response to received echo signals.

Sonographers manually adjust the gate location, gate size, transmit frequency and other spectral Doppler imaging control parameters in order to acquire a desirable image. This process may be tedious and inexact, resulting in suboptimal spectral Doppler imaging. For example, the desired location of the spectral Doppler gate is typically at a position associated with the maximum flow velocity. A user may inexactly position the range gate at a different, adjacent position. As another example, an initial transmit frequency is selected by the user by adjusting the transmit frequency to different values until the image is subjectively correct, but not necessarily optimal.

Some processes have been proposed for automatic placement of the spectral Doppler gate. For example, a two-dimensional Doppler image of energy or velocity information is acquired. A position within the two-dimensional image associated with the maximum velocity or energy is selected for positioning of the spectral Doppler gate. Another proposed algorithm also samples at a plurality of predefined locations. In particular, the spectral power is calculated at multiple predefined locations in a one, two or three-dimensional grid. The location with the greatest spectral power is selected for the spectral Doppler gate position. However, sampling at predefined locations, such as for a two-dimensional image, may require extra processing and time.

Other spectral Doppler parameters may be automatically set, such as the size of the gate, ideal line angle and point of origin on the transducer.

BRIEF SUMMARY

The present invention is defined by the following claims, and nothing in this section should be taken as a limitation on those claims. By way of introduction, the preferred embodiments described below include methods and systems for automatic optimization in spectral Doppler ultrasound imaging. The value for one or more spectral Doppler parameter is optimized using numerical optimization rather than predefined sampling. Various spectral Doppler parameters are set, such as a position of the gate, gate size, transmit frequency, filter settings, Doppler gain, beamline orientation or angle of intersection between the gate position and the scan line, aperture size, or other spectral Doppler transmit or receive parameters effecting the spectral Doppler imaging. A processor automatically calculates a setting or value for one or more of the spectral Doppler parameters, resulting in more objective optimization than provided by a user setting.

In a first aspect, a method for automatic optimization in spectral Doppler ultrasound imaging is provided. Multiple sequences of spectral Doppler pulses are fired into a patient. Multiple goal values are determined in response to the sequences. A change for a spectral Doppler parameter is estimated as a function of the goal values. The spectral Doppler parameter is set automatically as a function of the estimated change.

In a second aspect, a method for automatic optimization in spectral Doppler ultrasound imaging is provided. An initial spectral Doppler parameter value is received. The initial spectral Doppler parameter value is automatically altered to a second spectral Doppler parameter value. A third spectral Doppler parameter value is determined as a function of a numerical optimization of the initial and second spectral Doppler parameter values.

In a third aspect, a method for automatic optimization in spectral Doppler ultrasound imaging is provided. At least one Doppler pulse is fired into an identified region. At least one of the transmit frequency, filter settings and Doppler gain are automatically set in response to an echo signal from the Doppler pulse.

In a fourth aspect, a system for automatic optimization in spectral Doppler ultrasound imaging is provided. The system includes a transducer operative to fire sequences of spectral Doppler pulses. A processor is operative to determine multiple goal values in response to the sequences, to estimate a change of the spectral Doppler parameter as a function of the values and to automatically set the spectral Doppler parameter as a function of the estimated change.

In a fifth aspect, a method for automatic optimization in spectral Doppler ultrasound imaging is provided. Multiple sequences of spectral Doppler pulses are fired into a patient. Multiple goal values are determined in response to the sequences. Based on these goal values, zero or more iterations of the following acts are generated adaptively, generating an intermediate spectral Doppler parameter value based on previous calculated goal values.

firing a sequence corresponding to this spectral Doppler parameter value.

calculating the goal value in response to the sequence.

The resulting spectral Doppler parameter value is then determined based on the preceding calculated goal values.

Further aspects and advantages of the invention are discussed below in conjunction with the preferred embodiments.

BRIEF DESCRIPTION OF THE DRAWINGS

The components of the figures are not necessarily to scale, emphasis instead being placed upon illustrating the principles of the invention. Moreover, in the figures, like reference numerals designate corresponding parts throughout the different views.

FIG. 1 is a block diagram of one embodiment of a system for automatic optimization of spectral Doppler ultrasound imaging;

FIG. 2 is a flow chart diagram of one embodiment of a method for automatic optimization of spectral Doppler ultrasound imaging;

FIG. 3 is a graphical representation of one embodiment associated with setting a gate position and beamline orientation.

DETAILED DESCRIPTION OF THE DRAWINGS AND PRESENTLY PREFERRED EMBODIMENTS

Figure 4:
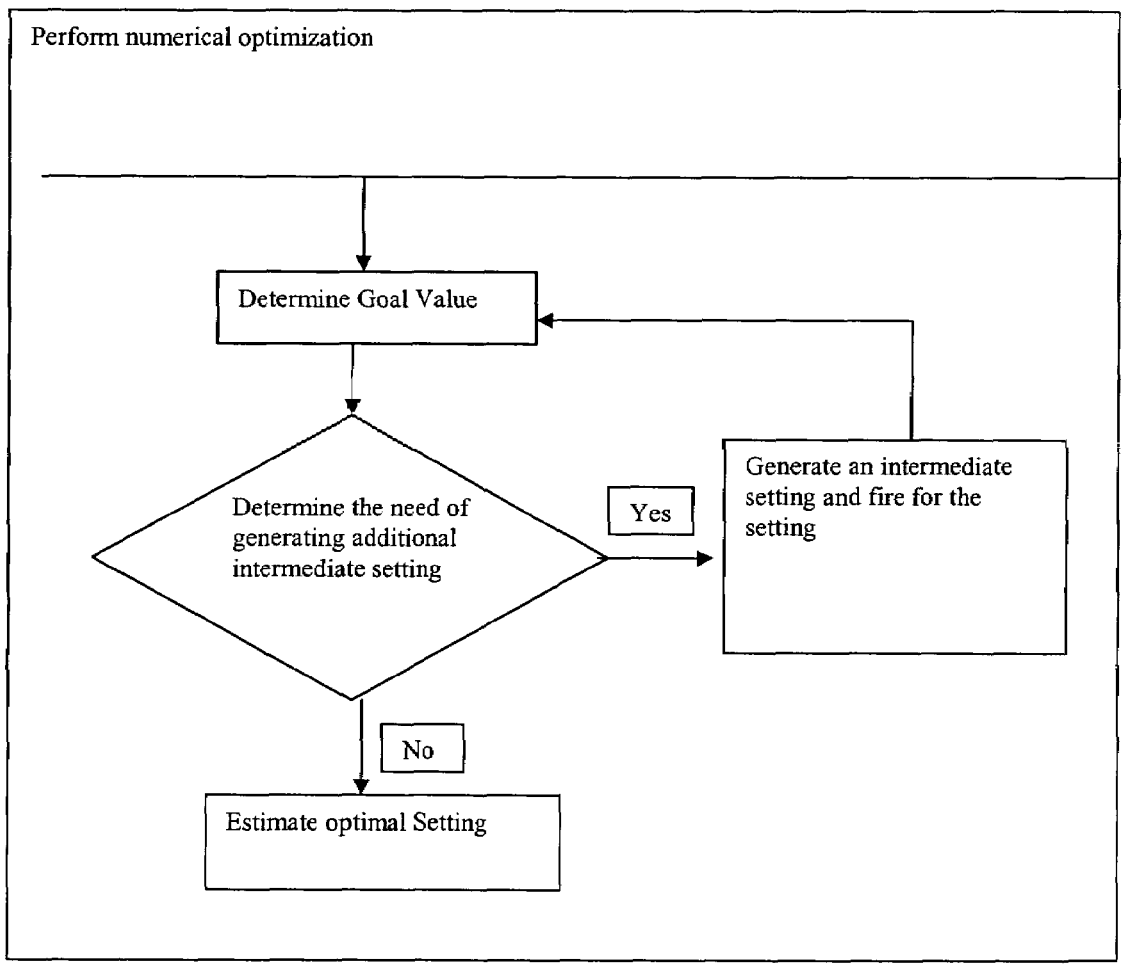
FIG. 4 is a flow chart diagram of one embodiment of an adaptive iterative process performed in the method of FIG. 2.

Spectral Doppler parameters (e.g. imaging control parameters) are optimally selected. The selection is automated to achieve different imaging goals for different applications. For example, the spectrum intensity is maximized by setting the gate location and beamline orientation. As another example, an area with the highest flow is located for a gate position. As yet another example, a gate position associated with valve regurgitation is located. The desired goal is expressed as a mathematical function to be optimized with respect to one or more of the spectral Doppler parameter. For example, the spectral intensity sum, spectral signal-to-noise ratio sum, spectral maximum velocity sum or other goal function is used to numerically optimize gate location, beamline orientation, transmit frequency, filter settings, Doppler gain, gate size, velocity baseline, scan line location, scan line angle or other spectral Doppler parameters.

FIG. 1 shows a system for automatic optimization in spectral Doppler ultrasound imaging. The system 10 includes a transmit beamformer 12, a transducer 14, a processor 16 and a display 18. Additional, different or fewer components may be provided. The system 10 is any now known or later developed spectral Doppler ultrasound imaging system, such as ultrasound systems manufactured by Siemens Medical Solutions USA, Inc.

The transmit beamformer 12 comprises a waveform generator, memory, digital signal processors, filters, delays, amplifiers, control processors, other digital components, other analog components and combinations thereof for generating sequences of Doppler pulses. Any now known or later developed transmit beamformer may be used. A transmit waveform, such as a single cycle or multi-cycle bipolar square wave or sinusoidal waveform is generated for each of a plurality of channels in an aperture with relative delays and apodization for focusing the ultrasound energy as a spectral Doppler pulse along a scan line. Unfocused or plane waves may also be generated. By setting any delays, apodization and aperture, the scan line position within a region may be changed as well as the origin of the scan line from the transducer 14 and angle of intersection of the scan line with the transducer 14. The delay and apodized waveforms generated by the transmit beamformer 12 are provided to the transducer 14.

The transducer 14 comprises a one-dimensional, two-dimensional or multi-dimensional transducer array of piezoelectric or microelectromechanical transducer elements. In alternative embodiments, a single element is provided for the transducer 14. The transducer 14 is operative to fire sequences of spectral Doppler pulses by transducing the electrical signals from the transmit beamformer into acoustical energy. The transducer 14 converts electrical waveform signals from the transmit beamformer 12 to acoustic energy for transmitting acoustic energy along a scan line. Some of the transmitted acoustic energy reflects off of structures and fluids. The reflected echoes are converted by the transducer 14 into electrical energy and provided to the processor 16.

The processor 16 comprises a receive beamformer, a spectral Doppler detector, a filter, amplifier, or other image processing device for converting receive echo signals into a spectral Doppler image. The processor 16 additionally or alternatively includes a control processor for managing the system 10 or components of the system 10. In one embodiment, the processor 16 comprises a digital signal processor, a general processor, an application specific integrated circuit, a digital processor, an analog processor or any other processor now known or later developed. Additional, different or fewer components may be provided for the processor 16.

In response to receive beamformed signals, Doppler detected signals, or image signals generated for a spectral Doppler imaging display, the processor 16 determines goal values, such as a goal value associated with multiple sequences of Doppler pulses. For example, a sequence of Doppler pulses is transmitted to generate information associated with one time for a spectral Doppler display, such as a velocity spectrum modulated as a function of energy for a given time. A goal value is calculated from the spectrum information for that time. Another goal value is calculated in response to a subsequent sequence of pulses. Based on these two goal values, zero or multiple iterations of the following acts are generated adaptively, generating an intermediate spectral Doppler parameter value based on previous calculated goal values.

firing a sequence corresponding to this spectral Doppler parameter value.

calculating the goal value in response to the sequence.

The resulting spectral Doppler parameter value is then determined based on the preceding calculated goal values.

The display 18 is a CRT, monitor, LCD, plasma screen, projector or other now known or later developed display for displaying a spectral Doppler image responsive to the set parameters. For a black and white spectral Doppler image, a range of velocities with each velocity modulated as a function of energy is provided as a function of time. The intensity of a given pixel or pixel region represents energy where velocity is provided on the vertical scale and time provided on the horizontal scale. Other image configurations may be provided, including colorized spectral Doppler images.

FIG. 2 shows a method for automatic optimization in spectral Doppler ultrasound imaging. One or more spectral Doppler parameters are numerically optimized. In one embodiment, the numerical optimization occurs without a full sampling of a one-, two-, or three-dimensional region. Only a few possible settings are sampled and a next possible setting is adaptively estimated or calculated. The spectral Doppler parameter is set based on mathematical calculation rather than comparison of multiple sampled settings. Various of the acts shown in FIG. 2 may be skipped, not provided or implemented in different ways. Additional or different acts may also be provided.

In act 30, an initial spectral Doppler parameter value is received. The value is received from memory, a processor, user input or combination thereof. For example, a user selects spectral Doppler imaging with a particular transducer 14 to be used. In response, the system 10 provides various initial spectral Doppler parameter values, such as a transmit frequency, gate size, filter settings and Doppler gain. As another example, the user indicates a gate position on a two-dimensional image and a processor determines transmit and receive beamformer settings for transmitting to and receiving from the selected gate position. The user or the processor 16 determines an initial scan line angle or beamline orientation relative to the selected gate position, such as the shortest line from the transducer 14 to the gate position or a line extending perpendicular from the transducer 14 to the gate position. An initial value is provided for each of the spectral Doppler parameters or imaging control parameters. Any of various users' settings, such as a gain control setting in response to a gain control knob or other configuration settings, provide the initial values. For example, the user places the Doppler gate in a vicinity of flow or most likely location of maximum flow and presses a button to activate automatic optimization. The initial settings correspond to the initially provided settings, such as the Doppler gate position, provided by the user. The software or algorithm discussed herein guides the Doppler gate as well as other spectral Doppler parameters to the proper depth and scan line orientations so as to obtain an optimal spectrum. Additional algorithm performance improvements can be achieved by restricting the valid search region for placing the Doppler gate to locations where color flow signals have previously been detected, or to locations within the B mode image which have intensities meeting threshold criteria. U.S. Pat. No. 6,176,830, the disclosure of which is incorporated herein by reference, shows such improvements.

In act 32, the initial spectral Doppler parameter value for one or more of the parameters is automatically altered to a different value. The alteration occurs as part of a numerical optimization. In one embodiment, an alteration predetermined for the type of parameter is provided. For example, a transmit frequency is altered in a 1 MHz step to be larger, but a different size step increasing or decreasing the frequency may be provided. As another example, a gate position is shifted by one gate size along a same scan line or to an adjacent scan line. Any of various predetermined or experimentally determined shifts and direction of a shift in each of the parameters or one of the parameters may be used. In other alternative embodiments, the shift size or direction are adaptive as a function of a value calculated in act 38 for the initial spectral Doppler parameter value.

In act 34, multiple sequences of spectral Doppler pulses are fired. One sequence is fired and a Doppler spectrum is determined in response to the initial spectral Doppler parameter values. A subsequent or other sequence of Doppler pulses is fired, and a Doppler spectrum is generated in response to the altered spectral Doppler parameter settings. Since at least one setting for at least one spectral Doppler parameter is different between the two firings, a different spectrum or different spectral Doppler information may result. In alternative embodiments, information from prior to generation of the spectrum is acquired in response to the different settings. The firings are along a same or different scan lines. In yet other alternative embodiments, a single firing of a Doppler pulse or a single sequence of Doppler pulses used for generating a single spectrum is provided without the alteration of act 32 or only for the altered settings of act 32. A sequence of Doppler pulses is provided for calculating or estimating the Doppler spectrum at a given time. Any number of transmitted pulses may be used for a sequence, including different numbers of transmitted pulses for sequential sequences of Doppler pulses.

In one embodiment, a value for a single spectral Doppler parameter is altered for optimization. In alternative embodiments, the values for two, more, a subset or all of the spectral Doppler parameters are altered between two sequences of Doppler pulses. The sequences of Doppler pulses may be separated by none, one or more other sequences of Doppler pulses or other ultrasound pulses for any purpose.

A subsequent spectral Doppler parameter setting is determined as a function of a numerical optimization of the initial and altered spectral Doppler parameter settings in act 36. In alternative embodiments, the subsequent spectral Doppler parameter value is determined as a numerical optimization of only the initial or only the altered spectral Doppler parameter value. In yet other alternative embodiments, additional alterations of one or more spectral Doppler parameters are provided for numerically optimizing a given spectral Doppler parameter value. By providing numerical optimization, the amount of samplings to determine an optimum value is reduced. Any of various spectral Doppler parameters are optimized individually, sequentially, or in parallel.

To perform the numerical optimization of act 36, goal values are determined in response to the fired sequences of Doppler pulses of act 34. For example, a resulting value responsive to the initial spectral Doppler parameter value is calculated, and another resulting value responsive to the altered spectral Doppler parameter value is calculated. Goal values responsive to any of the various combinations of settings of spectral Doppler parameters are calculated.

The resulting or goal value is calculated from any of various mathematical functions. In one embodiment, the resulting or goal values are calculated from a spectrum resulting from the firings and settings of acts 30-34. Detected information or image gray scale values are used. In alternative embodiments, the resulting or goal values are calculated from received data other than the calculated Doppler spectrum.

The goal value is calculated from a function to be optimized with respect to the spectral Doppler parameters, such as gate location, beamline orientation, gate size, transmit frequency, filter settings or Doppler gain. One energy function is the spectral intensity sum or sum of intensity or energy values for non-noise velocities at a given time or period. The spectral intensity sum is given by:

$$sis(x1, y1, \theta) = \sum_{v,t} |v| G(v, t)$$

where x and y provide the gate location, the $\theta$ is the beamline orientation, v is the velocities and $G(v, t)$ is the gray scale values for each velocity at a given time. (v,t) are all the points inside the chosen velocity (min_v, max_v) and time duration (min_t, max_t) window in the spectral display. The velocity may be squared or other spectral intensity functions may be used.

Another energy function is the spectral signal-to-noise ratio. The signal can be expressed as follows, $$\frac{\sum_{(v,t) \in X} G^2(v, t)}{\text{num of elements in set } X}$$

where X is a set of (v,t) points inside the chosen time duration and velocity window which has the value of G(v,t) greater than a certain threshold. The noise information is acquired by image processing or by receiving a frame of data without transmitting acoustic energy. Yet another function is a spectral maximum velocity sum as shown below.

$$\sum_t \max(\{v : v \in [\min\_v, \max\_v] \text{ and } G(v, t) > \text{threshold}\})$$

Means of energy, velocity or combination thereof are used in alternative embodiments. Any of various functions which may be minimized, maximized, thresholded or otherwise used to identify an optimal setting may be used. For example, pattern matching of the energy as a function of velocity of the spectrum is used. Correlation or other pattern matching algorithms are performed to provide an amount of match.

The function used to determine the goal value is the same or different for different spectral Doppler parameters. In one embodiment, gate location, beamline orientation and gate size are optimized using the spectral intensity sum. The transmit frequency is optimized using the spectral signal-to-noise ratio sum to obtain a maximum energy as a function of transmit frequency. The Doppler gain is set as a function of the spectral signal-to-noise ratio sum. The filter settings are also optimized as a function of the spectral signal-to-noise ratio sum. For example, the bandwidth of the clutter filter is altered to provide the maximum signal-to-noise ratio. Other filtering parameters for a clutter filter or other filter may be optimized. Different combinations of spectral Doppler parameter and optimization function are provided in other embodiments.

The function used for optimizing a particular spectral Doppler parameter differs in response to different types of spectral Doppler ultrasound imaging. For example, the location of the gate is optimized as a function of pattern matching for valve regurgitation imaging. A square shaped spectrum of energy as a function of velocity identifies an improper valve regurgitation. The system 10 and associated spectral Doppler imaging parameters, such as the location of the gate, are optimized to provide the spectrum most resembling a square shape so that the worse case is identified for comparison or diagnosis.

Goal values are calculated for a discrete time or over a time duration. For example, the spectral intensity sum is calculated for optimizing the gate position, beamline orientation and/or gate size over one or more heart cycles. Different time periods may be used. In one embodiment, the heart cycle is calculated for identifying the time duration. In other embodiments, a time period is selected that is associated with a typical heart cycle. Other parameters for input to the optimization function may be varied or set, such as the velocity window. In one embodiment, the velocity window for identifying signal from noise in a spectral Doppler image is used. In other embodiments, a greater or lesser threshold is used for calculating the goal value.

In act 40, a new setting of the spectral Doppler parameter value is estimated. The setting is adaptively based on the calculated goal values. A change of the spectral Doppler parameter value or setting is estimated. The change is estimated either as a difference from a current setting or as an absolute value that is different than the current setting. The change is estimated for any one or more of the spectral Doppler parameters discussed above, such as transmit frequency, gate position, filter settings, Doppler gain, angle of the scan line through a gate position (beamline orientation) and combinations thereof.

A numerical optimization searching technique is used to maximize the goal values. In alternative embodiments, the goal value is minimized or otherwise thresholded. Any of various numerical searching techniques now known or later developed are used, such as in multi-dimensional case, Gradient Descent method, Conjugate Gradient method, Newton or Quasi-Newton method, in one dimensional case, Parabolic fitting method, Brent's method, Brent with first derivative method or Newton numerical optimization. For example, rather than performing an exhaustive search by sampling a plurality of locations within a region, as in Gradient Descent method, a derivative is used to identify a likely value or setting of the spectral Doppler parameter from previous settings. A gradient of the current setting provides a search direction of a future setting. If one of the altered settings of act 32 resulted in the goal value being worse, the setting is altered in an opposite direction. As shown in FIG. 4, given the search direction, the numerical routine automatically and iteratively generates zero or more immediate spectral Doppler parameter settings based on the goal values calculated with the preceding settings. As a result of each numerical optimization, a goal value is calculated. The need for generating additional intermediate settings of the Doppler parameter is determined, such as by comparison to a threshold indicating an optimal setting. If no more intermediate settings are to be calculated, then an optimal setting is estimated by selecting the setting associated with the desired goal value. If additional intermediate settings are to be calculated, then the next setting is estimated from the numerical optimization. Pulses are fired using the next setting and the process repeats by calculating another goal value. As a result, the optimal setting along the search direction is determined based on the preceding calculated goal values. When the desired value is a maximum value, a negative representation may be used to obtain minima for numerical searching techniques. In alternative embodiments, only one of direction or magnitude is altered.

For example, the Doppler gate steering angle or beamline orientation varies from −20 to 20 degrees. Starting at zero degrees, numerical optimization may adjust the steering angle to maximum possible extent, such as −20 degrees in only 2, 3, 4, or any other low number of iterations. An exhausted sub-sampling may require 40 samples at one degree increments.

The new spectral Doppler parameter setting for one or more parameters is used to transmit and receive ultrasound energy. A goal value is calculated based on the most recent information. The numerical searching is then repeated to identify a next setting. The operation is repeated until a local maxima or local minima is identified. In alternative embodiments, a threshold is applied to the magnitude of change to indicate a sufficient maxima or minima without identifying an exact maxima or minima setting. Other algorithms may be used for ending the numerical optimization, such as a reversal of direction in the derivative or gradient associated with a sufficiently small magnitude change.

In one embodiment, the gradient direction is associated with a two-dimensional plane, such as for the gate position. Three or more goal values and associated initial and alternate settings may be used to provide a two-dimensional gradient direction or vector. Other values, such as the beamline orientation, transmit frequency, Doppler filter settings, and Doppler gain, are numerically optimized using initially two or more different settings. For three-dimensional imaging, additional settings may be used for gate position numerical optimization.

In one embodiment, the spectral Doppler parameters are numerically optimized sequentially. For example, a gate location or position is optimized, and then the beamline orientation or angle of incidence to the gate location is optimized subsequently. The parameters are optimized in any of various possible orders.

In alternative embodiments, two or more spectral Doppler parameters are optimized substantially simultaneously, such as using an energy or goal function that depends on two different spectral Doppler parameters. For example, the gate depth and beamline orientation relative to the gate location (i.e. angle of incidence) are optimized as part of the same function. An initial depth and orientation are received. A sample is then acquired at a different depth with the same orientation, and a subsequent sample is obtained with a different orientation but a same depth as the initial depth. The spectral intensity sum is calculated for each of the three samples. The derivative or gradient associated with each of the parameters is calculated and provides one axis of a two-dimensional vector representation. The resulting gradient direction provides a search direction for a better gate depth and orientation setting. Zero or multiple iterations of steps generate, adaptively, which includes generating intermediate settings along the search direction and calculating the corresponding goal value as part of the numerical optimization. Then, the optimal setting along the search direction can be determined based on the preceding calculated goal values. To further optimize the setting, the above process is repeated to obtain a new gradient direction at the current best setting and thus determine the next best setting. In the above example, the gradient provides a search direction of a desired setting for each of the gate depth and orientation in a two-dimensional space corresponding to gate depth and orientation. The two-dimensional vector identifies a subsequent gate position and orientation as part of the numerical optimization. Other vector processes may be used. Multivaried functions accounting for two or more spectral Doppler parameters is numerically optimized without requiring subsampling of predefined locations using a plurality of different settings and combinations. Energy or goal functions that are a multiplication, addition, subtraction, division or other mathematical combination of information associated with two different parameters may be used.

FIG. 3 shows an initial gate position 50 associated with a scan line 52 perpendicular to the transducer 14. As part of either sequential or simultaneous sampling for numerical optimization, the gate position is shifted to a position shown at 54 along a different scan line 56. The beamline orientation or angle of incidence to the gate position 50 is also shifted as represented by scan line 58. Using numerical optimization, the gate position may be determined as position shown at 60 along the same scan line 52 that is normal to the transducer 14. Other positions and scan line orientations may be provided.

Altering settings of one spectral Doppler parameter are used to set a different spectral Doppler parameter in one embodiment. For example, the bandwidth of a clutter filter is set by altering the beamline orientation or angle of incidence. A spectrum is obtained for two different angles of incidence. The two spectra are compared. The bandwidth of the filter is set at a frequency associated with the divergence on the low frequency end of the spectra from each other. The similar low frequency information represents clutter to be filtered out. Where only flow information is available in each spectra, the spectra may be different for all low frequencies. As a result, the bandwidth of the Doppler clutter filter is set to zero or the low frequency noise cut off of the spectra.

In act 42, the spectral Doppler parameter is set as a function of the estimated change from the numerical optimization. The processor 16 sets the spectral Doppler parameter without user input other than an initial setting. The numerical optimization is also performed automatically. The resulting value is used for subsequent imaging or further numerical optimization. Where more than one spectral Doppler parameter is being set sequentially, the process automatically repeats until some or all spectral Doppler parameters have been set. Where two or more spectral Doppler parameters are set substantially simultaneously, such as a function of a vector, the final vector identifying a maxima, minima or sufficiently close maxima or minima identifies the final settings of the spectral Doppler parameters. The final setting of the spectral Doppler parameters is the same or different than the initial or any subsequent settings. For example, a numerical optimization may follow a trend in a setting to the maxima and then determine the additional sample or samples following a trend away from the maxima in order to identify the maxima. As another example, the initial user settings may correctly identify the maxima as confirmed by numerical optimization.

In act 44, a spectral Doppler display is generated using the automatically set spectral Doppler parameter values. A spectral Doppler image is generated during the numerical optimization in response to the various settings in one embodiment, but may be generated only after the settings are numerically optimized in other embodiments. Alternatively, the initial settings are used for generating a spectral Doppler image until numerically optimized settings are available.

The optimized spectral Doppler parameter settings are used for an imaging session or until the user resets one or more of the imaging controls affecting a spectral Doppler parameter setting. In alternative embodiments, one, a subset or all of the spectral Doppler parameters are optimized periodically regardless of user input or are optimized in response to a user request for optimization. Any of various periods may be used, such as every heart cycle, every second, or every minute. Optimization is triggered in other embodiments by events, such as the detection of tissue movement relative to the transducer, a heart cycle event, a breathing cycle event, or other detected parameter.

Automatic optimization of spectral Doppler parameters for ultrasound imaging are provided in another embodiment with or without numerical optimization. At least one Doppler pulse is fired into an identified region. A sequence of Doppler pulses associated with determining a spectrum at one time or a plurality of sequences of Doppler pulses may be used. The region is identified by a user by positioning a region of interest, identifying a range gate position or by positioning a transducer relative to the patient. The system may identify a region using numerical optimization, thresholding, border detection or other fluid detection algorithms and devices. Transmit frequency, filter settings or Doppler gain are automatically set in response to echo signals from the firing. The automatic setting is responsive to numerical optimization, sampling and comparison, or other now known or later developed optimization techniques. In one embodiment, numerical optimization is used so that the setting is estimated from one or more previous settings using a numerical function. The Doppler parameter of transmit frequency filter setting or Doppler gain is automatically set as a function of the estimated setting. In alternative embodiments, sample and comparison is used where a region is sampled or subsampled at predefined values and resulting values associated with each location or possible variation of the spectral Doppler parameter are compared to identify a maxima or minima value without numerical optimization.

As an alternative to a gradient or vector based numerical optimization, a numerical optimization using optimized search patterns may be used. For example, a plurality of locations around an initial setting are sampled. The maxima or minima of the sample locations is selected and a search is then repeated using the new setting. As yet another alternative, a subsampling with one magnitude or spacing is provided. Lesser magnitude changes are then implemented as the process repeats for each identified maxima or minima. These refined searching techniques provide numerical optimization without using a mathematical formula for estimating the change in a setting. The change in a setting is estimated by the search pattern.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for automatic optimization in spectral Doppler ultrasound imaging, the method comprising:

(a) firing at least first and second sequences of spectral Doppler pulses;

(b) determining at least first and second goal values in response to the first and second sequences, respectively;
(c) estimating a change of a spectral Doppler parameter from the first and second goal values; and
(d) automatically setting the optimal spectral Doppler parameter as a function of the estimated change;
wherein (a) comprises transmitting the first sequence in response to a first setting of the spectral Doppler parameter and transmitting the second sequence in response to a second setting of the spectral Doppler parameter, the first setting different than the second setting, and (d) comprises automatically setting the spectral Doppler parameter at a third setting the same or different than one or both of the first and second settings.

2. The method of claim 1 wherein (c) comprises estimating the change of the spectral Doppler parameter selected from the group of: transmit frequency, gate position, filter setting, Doppler gain, angle of scan line for a gate position and combinations thereof and (d) comprises automatically setting the spectral Doppler parameter selected from the group above for (c).

3. The method of claim 2 wherein (c) comprises estimating the change of the gate position and wherein (d) comprises automatically setting the gate position.

4. The method of claim 2 wherein (c) comprises estimating the change of the Doppler gain and wherein (d) comprises automatically setting the Doppler gain.

5. The method of claim 2 wherein (c) comprises estimating the change of the filter setting and wherein (d) comprises automatically setting the filter setting.

6. The method of claim 1 wherein (b), (c) and (d) comprise numerically optimizing the spectral Doppler parameter without full sampling of a one or higher dimensional region.

7. The method of claim 1 further comprising:
(e) generating a spectral Doppler display in response to the spectral Doppler parameter set in act (d).

8. The method of claim 1 wherein (c) comprises estimating a vector corresponding to two different spectral Doppler parameters and (d) comprises setting both spectral Doppler parameters as a function of the vector.

9. The method of claim 1 wherein (b) comprises determining the first and second goal values as spectral intensity sums.

10. The method of claim 1 wherein (b) comprises determining the first and second goal values as spectral signal-to-noise sums.

11. The method of claim 1 wherein (b) comprises determining each of the first and second goal values over at least a one heart cycle period, the first goal value corresponding to a different heart cycle than the second goal value.

12. The method of claim 1 wherein (c) comprises adaptively performing zero or more iterations of the following acts based on the first and second goal values;
(c1) generating an intermediate spectral Doppler parameter setting based on previous calculated goal values;
(c2) firing a sequence corresponding to the intermediate spectral Doppler parameter; and
(c3) calculating a third goal value in response to the sequence; and
wherein (d) comprises automatically setting the optimal spectral Doppler parameter based on the preceding calculated goal values.

13. A method for automatic optimization in spectral Doppler ultrasound imaging, the method comprising:
(a) firing at least two Doppler Pulses into an identified region;
(b) automatically setting transmit frequency, filter settings or combinations thereof in response to an echo signal from (a); and
(c) estimating a first setting from previous settings, at least one of the previous settings being different from another of the previous settings;
wherein (b) comprises automatically setting as a function of the estimated first setting.

14. A system for automatic optimization in spectral Doppler ultrasound imaging, the system comprising:
a transducer operative to fire at least first and second sequences of spectral Doppler pulses, the first sequence being different from the second sequence; and
a processor operative to determine at least first and second values in response to the first and second sequences, respectively, estimate a change of a spectral Doppler parameter as a numerical optimization function of the first and second values, and automatically set the spectral Doppler parameter as a function of the estimated change.

15. The system of claim 14 wherein the processor is operative to estimate the change by adaptively generating zero or more of iterations of acts which include one or more of: generating intermediate spectral Doppler parameter setting based on the preceding calculated values, to instruct the transducer to fire the corresponding sequence of spectral Doppler pulses and compute the intermediate goal value, and to automatically set the optimal spectral Doppler parameter value based on the preceding calculated values.

16. A method for automatic optimization in spectral Doppler ultrasound imaging, the method comprising:
(a) firing at least first and second sequences of spectral Doppler pulses, the first sequence being different from the second sequence;
(b) determining at least first and second goal values in response to the first and second sequences, respectively;
(c) adaptively performing zero or more iterations of the following acts based on the first and second goal values;
(c1) generating an intermediate spectral Doppler parameter setting based on previous calculated goal values;
(c2) firing a sequence corresponding to the intermediate spectral Doppler parameter; and
(c3) calculating a third goal value in response to the sequence; and
(d) automatically setting an optimal spectral Doppler parameter based on the preceding calculated goal values.

* * * * *